（12） United States Patent
Schmieding et al.

(10) Patent No.: US 7,637,910 B2
(45) Date of Patent: Dec. 29, 2009

(54) METHOD OF ACL RECONSTRUCTION USING DUAL-SIDED ROTARY DRILL CUTTER

(75) Inventors: Reinhold Schmieding, Naples, FL (US); John Schelter, Naples, FL (US)

(73) Assignee: Arthrex, Inc., Naples, FL (US)

( * ) Notice: Subject to any disclaimer, the term of this patent is extended or adjusted under 35 U.S.C. 154(b) by 220 days.

(21) Appl. No.: 11/723,511

(22) Filed: Mar. 20, 2007

(65) Prior Publication Data

US 2007/0250067 A1 Oct. 25, 2007

Related U.S. Application Data

(60) Provisional application No. 60/783,839, filed on Mar. 21, 2006.

(51) Int. Cl.
*A61B 17/00* (2006.01)
(52) U.S. Cl. .......................... 606/80; 606/88; 623/13.12
(58) Field of Classification Search .................. 606/79, 606/80, 86, 86 R, 88, 96–98, 321; 623/13.11, 623/13.12, 13.14
See application file for complete search history.

(56) References Cited

U.S. PATENT DOCUMENTS

| 5,211,647 | A | | 5/1993 | Schmieding |
| 5,269,786 | A | | 12/1993 | Morgan |
| 5,320,626 | A | | 6/1994 | Schmieding |
| 5,350,380 | A | | 9/1994 | Goble et al. |
| 5,350,383 | A | | 9/1994 | Schmieding et al. |
| 5,603,716 | A | | 2/1997 | Morgan et al. |
| 6,015,411 | A | * | 1/2000 | Ohkoshi et al. ............... 606/80 |
| 6,149,654 | A | * | 11/2000 | Johnson ........................ 606/80 |
| 2004/0199166 | A1 | | 10/2004 | Schmieding et al. |
| 2004/0238154 | A1 | * | 12/2004 | Wirth et al. .................. 164/519 |

* cited by examiner

*Primary Examiner*—Thomas C Barrett
*Assistant Examiner*—Andrew Yang
(74) *Attorney, Agent, or Firm*—Dickstein Shapiro LLP

(57) ABSTRACT

Methods and apparatus for arthroscopic tenodesis using sockets in bone created by retrograde cutting. A dual-sided rotary drill cutter is used to form a tibial and femoral socket by retrograde and antegrade cutting, respectively. The method is used to form a pair of sockets in the joint, which accept the respective ends of a replacement graft. The dual-sided cutter is configured such that it cuts in both directions (retrograde and antegrade) and does not need to be flipped over between forming the respective sockets.

3 Claims, 26 Drawing Sheets

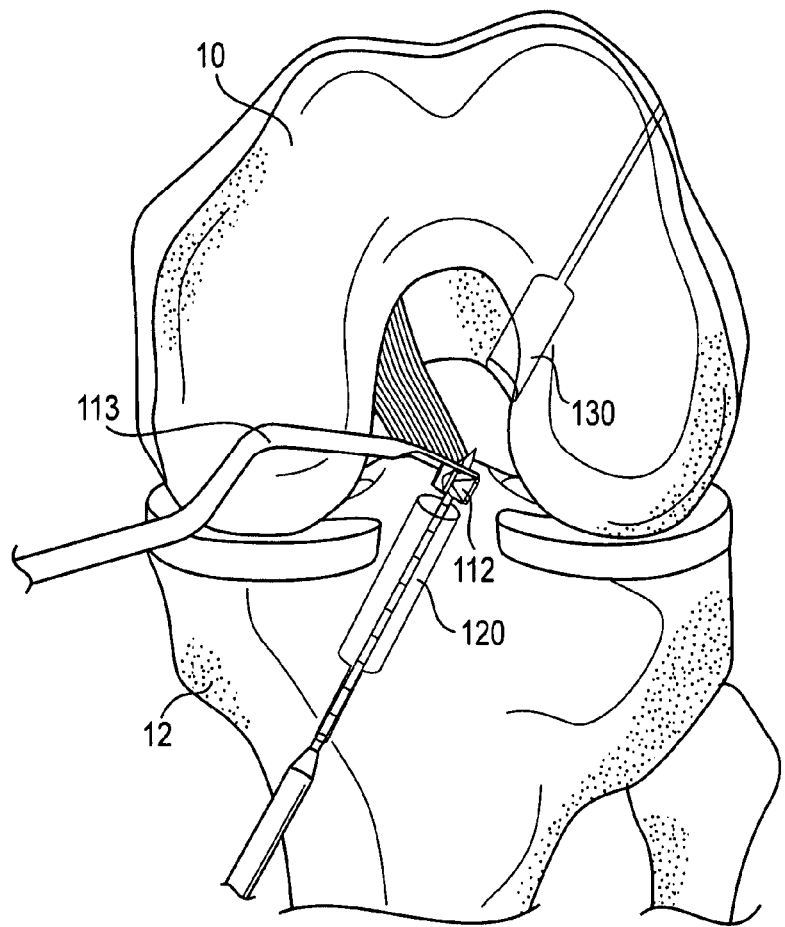
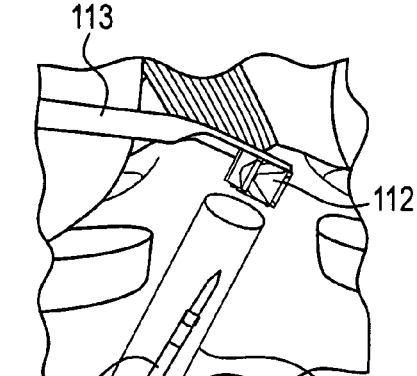
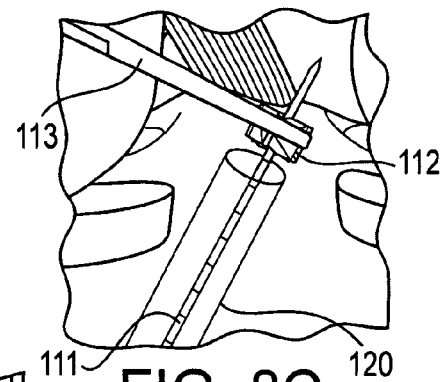
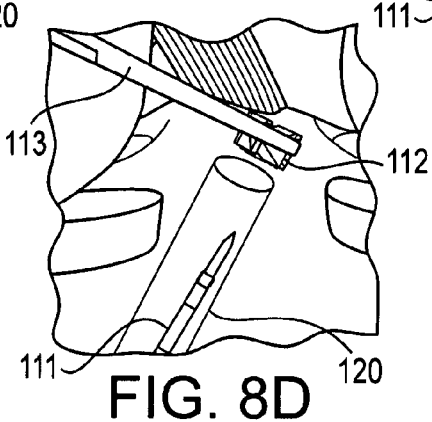
FIG. 8A
FIG. 8B
FIG. 8C
FIG. 8D

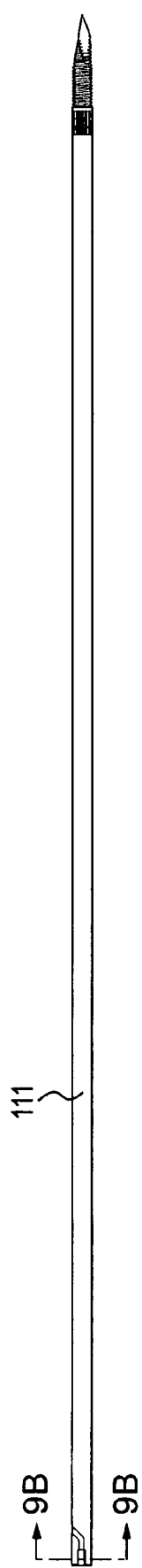
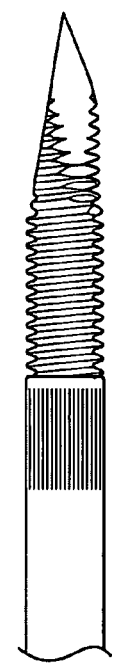
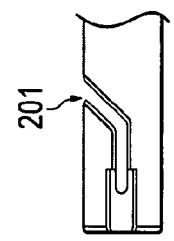
FIG. 9A
FIG. 9D
FIG. 9C
FIG. 9B

METHOD OF ACL RECONSTRUCTION USING DUAL-SIDED ROTARY DRILL CUTTER

CROSS REFERENCE TO RELATED APPLICATIONS

This application claims the benefit of U.S. Provisional Application No. 60/783,839, filed Mar. 21, 2006. This application is also related to U.S. application Ser. No. 10/803,044, filed Mar. 18, 2004 and U.S. application Ser. No. 11/598,093, filed Nov. 13, 2006, the entireties of which are incorporated herein by reference.

FIELD OF THE INVENTION

The present invention relates to the field of surgery and, more particularly, to methods of reconstructive knee surgery.

BACKGROUND OF THE INVENTION

Methods of anterior cruciate ligament (ACL) reconstruction (tenodesis) using interference screw fixation are described, for example, in U.S. Pat. Nos. 5,211,647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like. Accurate positioning of the tibial and femoral tunnels is accomplished using a drill guide, examples of which are disclosed in U.S. Pat. Nos. 5,269,786 and 5,350,383, incorporated herein by reference.

One drawback of the described tenodesis methods is that forming the tibial tunnel involves removal of significant amounts of bone material. U.S. Pat. No. 5,603,716 to Morgan et al. discloses a technique for ACL reconstruction that avoids the above-noted problem by forming sockets in both the femur and the tibia using a coring bone harvester. The harvester is impacted into bone to a desired depth so that bone material collects as a bone core within the harvester tube. The bone core is extracted from the bone socket using a simultaneous twisting and pulling motion. Such harvesting of bone cores in the joint is technically difficult.

Accordingly, the need exists for a method of ACL reconstruction that provides tibial socket formation without the need for extracting a bone core to form a bone socket. U.S. Patent Application Publication No. 2004/0199166, entitled ACL RECONSTRUCTION TECHNIQUE USING RETRO-DRILL (commonly assigned to Arthrex, Inc.) proposes a solution using a rotary drill technique such that the tibial and femoral sockets need not extend completely through the bone. However, in this technique, the cutter used must be removed within the joint cavity and flipped around in order to form the second socket. An improved method of forming these types of retrograde drilled sockets is desired.

SUMMARY OF THE INVENTION

The present invention overcomes the disadvantages of the prior art and fulfills the needs noted above by providing techniques and apparatus for creating bone sockets by drilling in a retrograde manner. The present invention advantageously utilizes a dual-sided rotary drill cutter to cut both the tibial and femoral sockets. The dual-sided rotary drill cutter has the advantage of being able to cut in both directions, thus is need not be flipped around within the joint cavity between drilling of the tibial and femoral sockets, as required in U.S. Patent Application Publication No. 2004/0199166.

An exemplary embodiment includes inserting a guide pin through the tibia, attaching a dual-sided cutter to the guide pin, forming a tibial socket in the tibia by retrograde drilling, forming a femoral socket in a femur by antegrade drilling, wherein the dual-sided cutter is not removed from the guide pin between formation of the respective sockets, and securing the ends of a graft respectively in the sockets of the tibia and femur.

Other features and advantages of the present invention will become apparent from the following description of the invention which refers to the accompanying drawings.

BRIEF DESCRIPTION OF THE DRAWINGS

FIGS. 8A-8D schematically illustrate the removal of the dual-sided rotary drill cutter in accordance with the present invention.

FIGS. 9A-9D illustrate a rotary drill guide pin in accordance with the present invention.

DETAILED DESCRIPTION OF THE INVENTION

The present invention provides rotary drill techniques and a dual-sided rotary drill apparatus for forming femoral and tibial bone sockets in a retrograde manner during ligament reconstruction, for example, anterior cruciate ligament (ACL) reconstruction.

Figure 19:
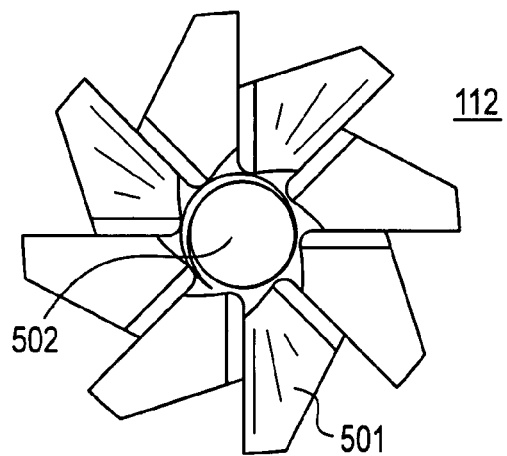
FIGS. 19-21 illustrate a dual-sided rotary drill cutter in accordance with the present invention.
Figure 20:
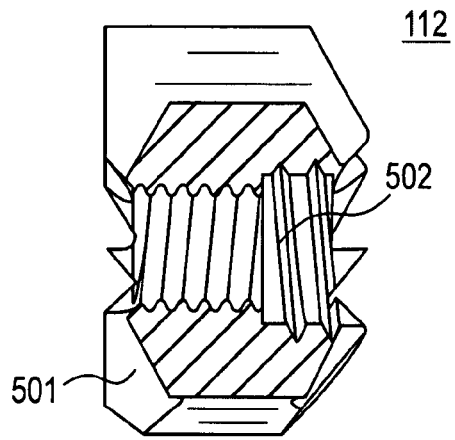
Figure 21:
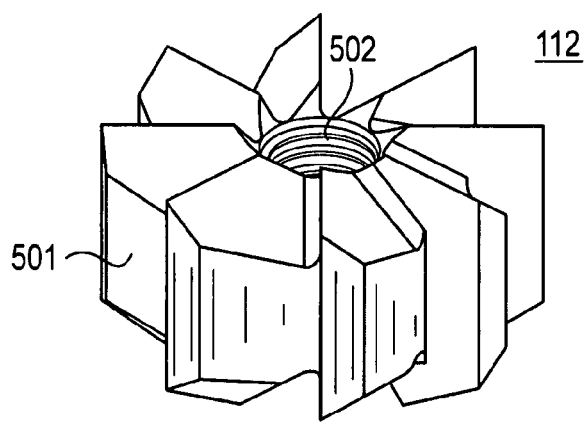

Referring now to the drawings, where like elements are designated by like reference numerals, FIGS. 19-21 illustrate a dual-sided rotary drill cutter 112. The rotary drill cutter 112 features a cylindrical body having a plurality of cutting teeth 501 radiating symmetrically. Advantageously, the dual-sided retrocutter 112 of the present invention has cutting teeth 501 on both sides of the cutter 112. Rotary drill cutter 112 is provided in a selected diameter corresponding to graft size, as discussed further below. The front and back cutting flutes 501 are arranged to facilitate all-inside tibial and femoral socket drilling, as discussed in more detail below. The cutter 112 also includes a threaded cannulation 502. The threads are configured such that the cutter 112 may be simultaneously disengaged from a threaded insertion post while being engaged to the rotary drill guide pin. As can be seen most clearly in FIG. 20, the cannulation 502 of cutter 112 contains two sets of threads, arranged in opposite directions.

An exemplary method of using the rotary drill cutter 112 to create tibial and femoral sockets, 120 and 130 respectively, is described below with reference to FIGS. 1-8, which illustrate a schematic anterior view of a knee in which ACL reconstruction is performed according to the present invention. In the following embodiment, a tibial socket 120 is formed in tibia 11 and a femoral socket 130 is formed in femur 10.

Figure 1A:
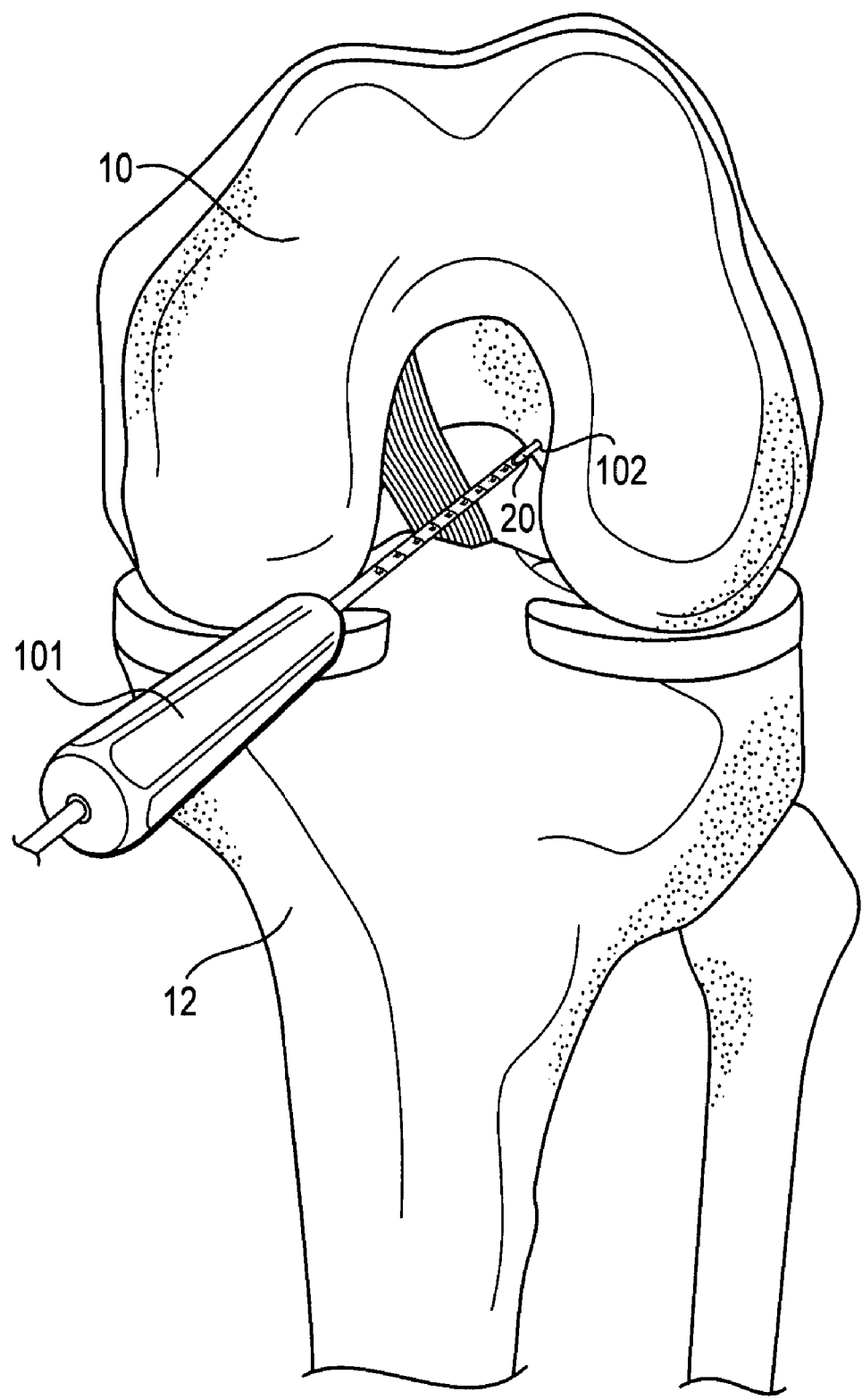
FIGS. 1A-1B illustrate an offset transtibial drill guide used in accordance with the present invention.
Figure 1B:
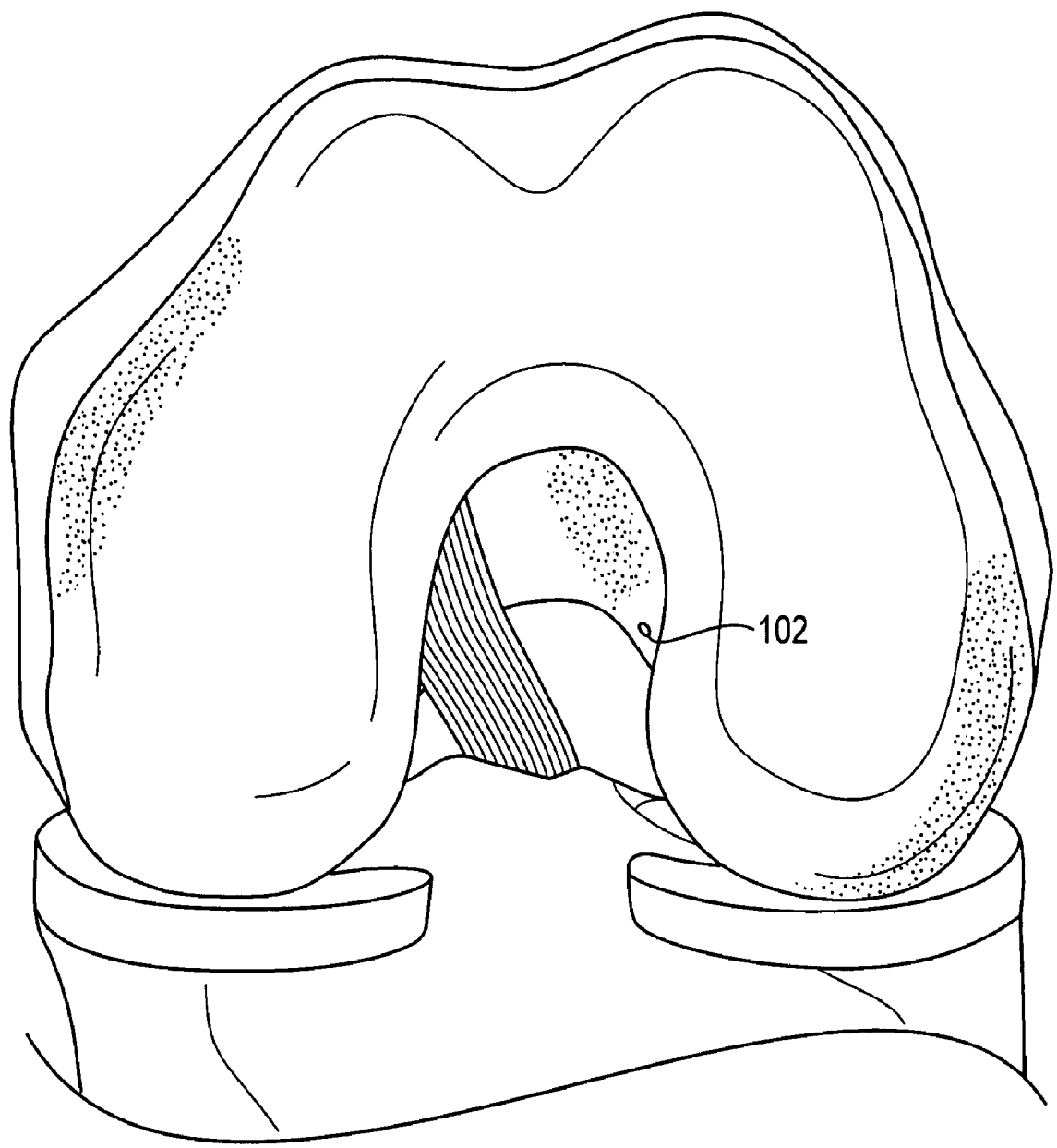

Before ligament reconstruction, all associated knee pathology is treated and an arthroscopic notchplasty is performed in routine fashion. Then, as shown in FIG. 1A, femoral tunnel alignment is obtained using the appropriately sized offset transtibial femoral ACL drill guide 101. The transtibial drill guide 101 is introduced through the anteromedial portal and placed in the over the top position that most closely replicates the anatomical origin of the PL bundle of the ACL. A beath pin 20 is inserted into the transtibial drill guide 101 and malleted or drilled approximately 5 mm into the femur 10 to create a reference position 102 for drilling. The reference position 102 is shown in FIG. 1B in more detail. The transtibial drill guide 101 is then removed.

Figure 2:
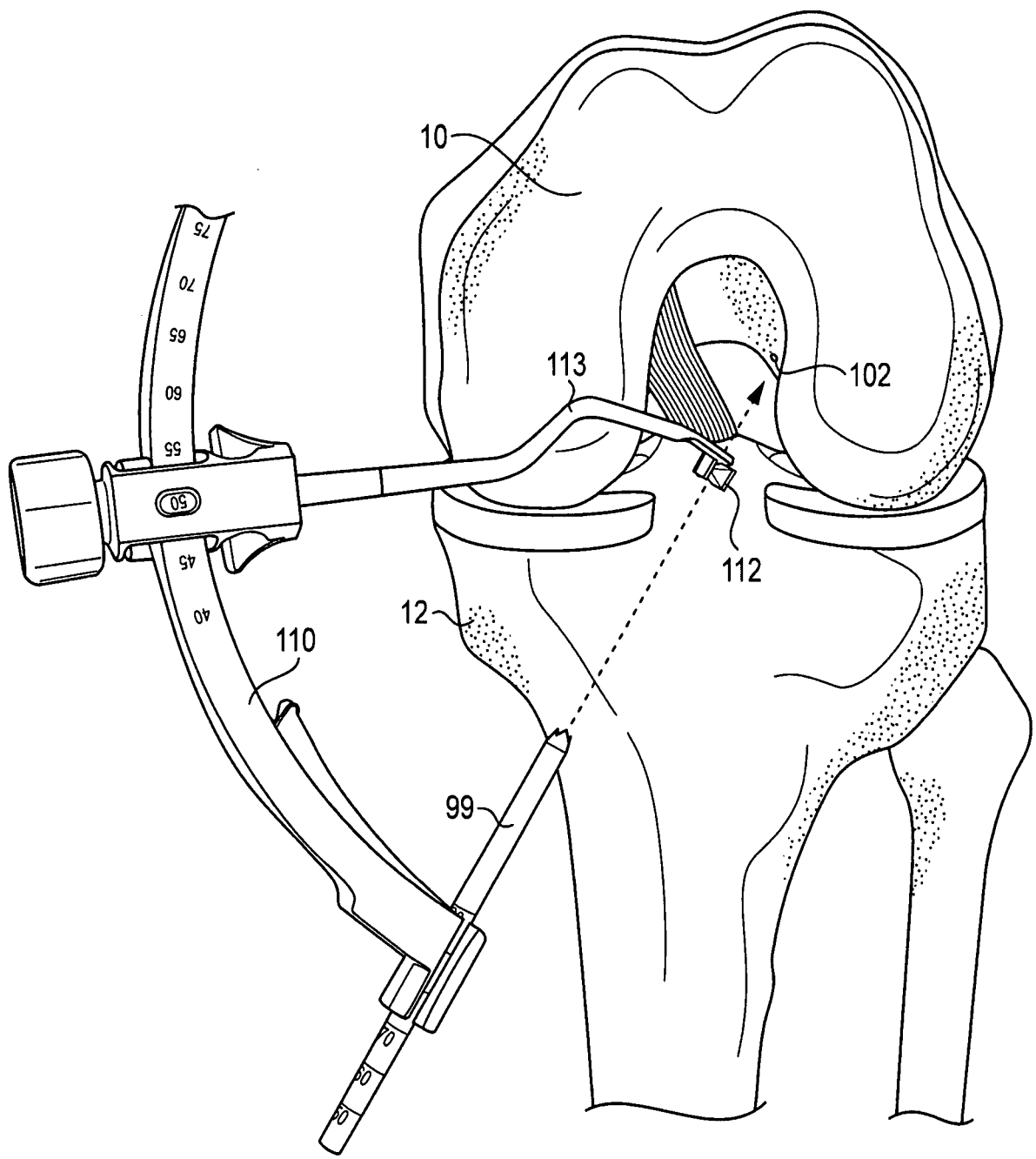
FIG. 2 schematically illustrates the insertion of a rotary drill guide pin in accordance with the present invention.
Figure 3A:
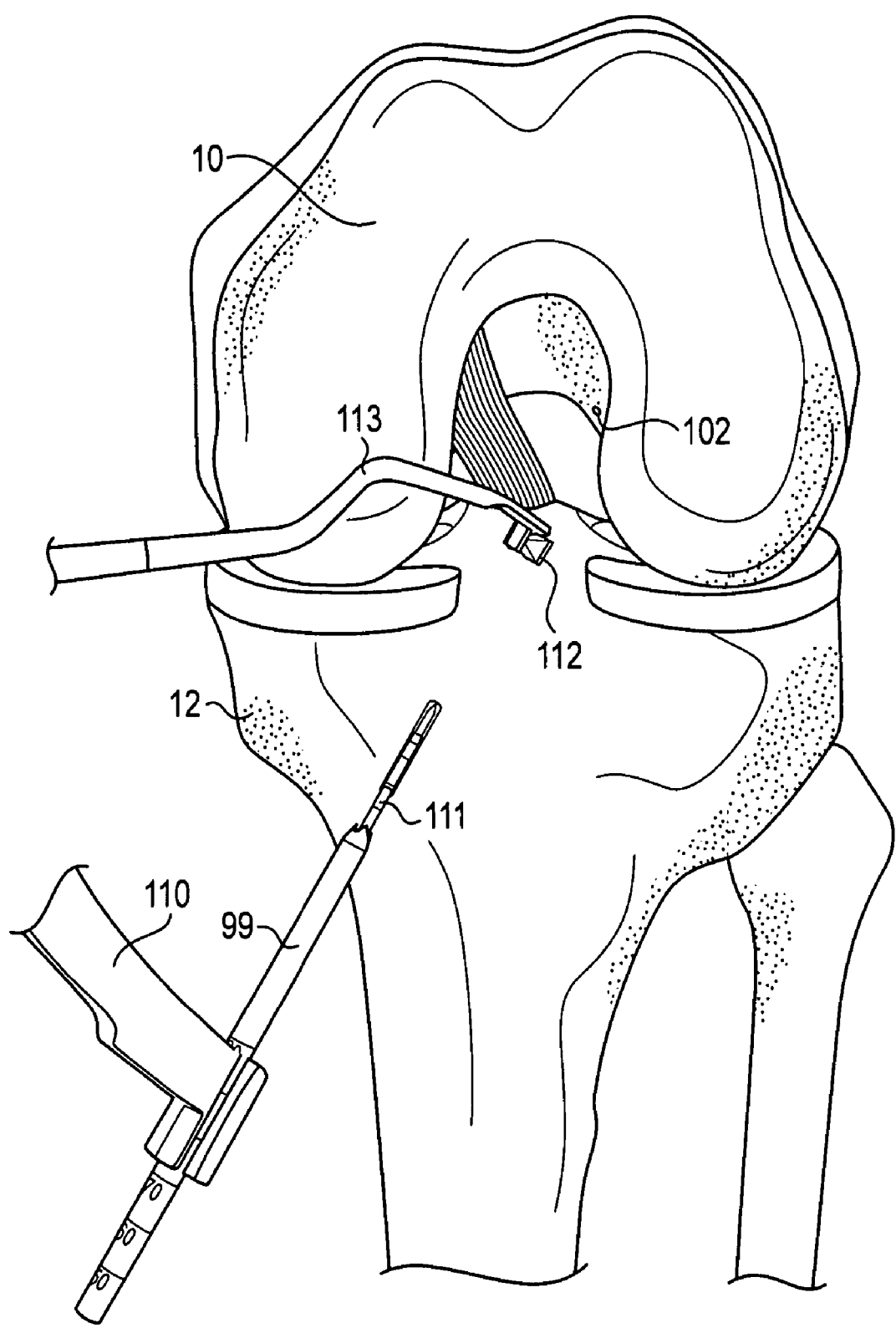
FIGS. 3A-3C schematically illustrate the insertion of a dual-sided rotary drill cutter in accordance with the present invention.

As shown in FIG. 2, a tibial ACL drill guide 113 is placed onto a drill guide C-ring 110 and the C-ring 110 is set to match the guide angle. The appropriate sized dual retrocutter 112 is attached to the tibial guide 113. The dual retrocutter 112 is placed over the tibial ACL footprint with the top of the cutter 112 aiming at the reference position 102. A drill sleeve 99 in inserted through a small incision and advanced to bone. Then, as shown in FIG. 3A, the rotary drill guide pin 111 is advanced (through the drill sleeve 99) through the tibia 12. In preferred embodiments, the rotary drill guide pin 111 is 3 mm in diameter and is drilled into the ACL approximately 7 mm anterior to the PCL.

Figure 3B:
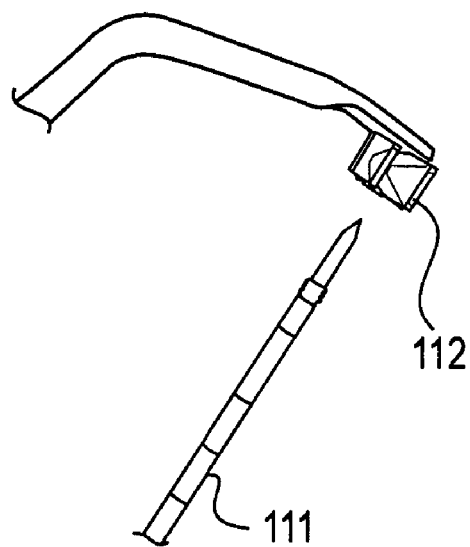
Figure 3C:
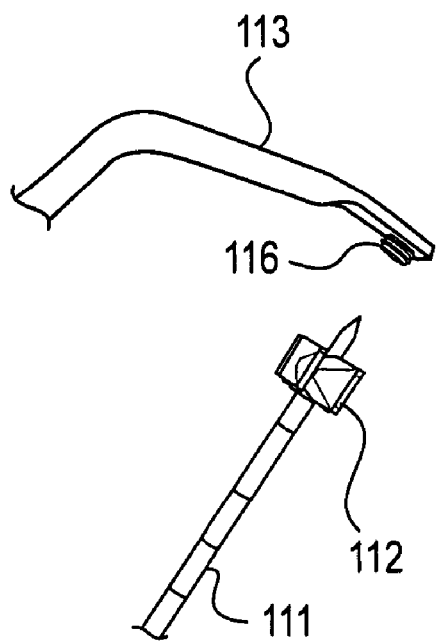

Then, as shown in FIGS. 3B and 3C, the dual rotary drill cutter 112 is attached to the guide pin 111. Slow forward drilling of the guide pin 111 engages the cutter 112 onto the rotary drill guide pin 111 and simultaneously disengages the cutter from the threads 116 of the insertion post 113. The two sets of internal threads on the cutter 112 are arranged such that this exchange is possible, as shown in FIG. 20. As previously discussed, FIGS. 19-21 illustrate the dual retrocutter 112 in more detail.

Figure 4A:
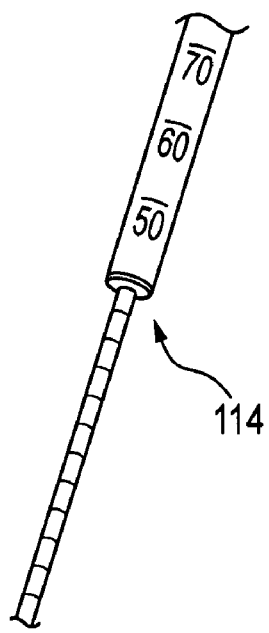
FIGS. 4A-4B illustrate a guide pin sleeve in accordance with the present invention.
Figure 4B:
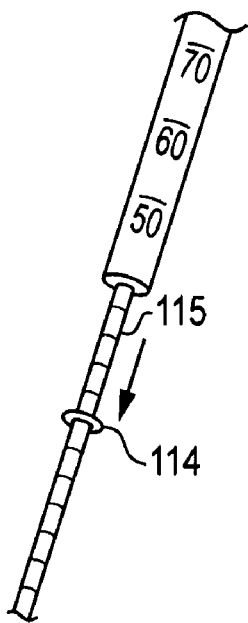
Figure 5:
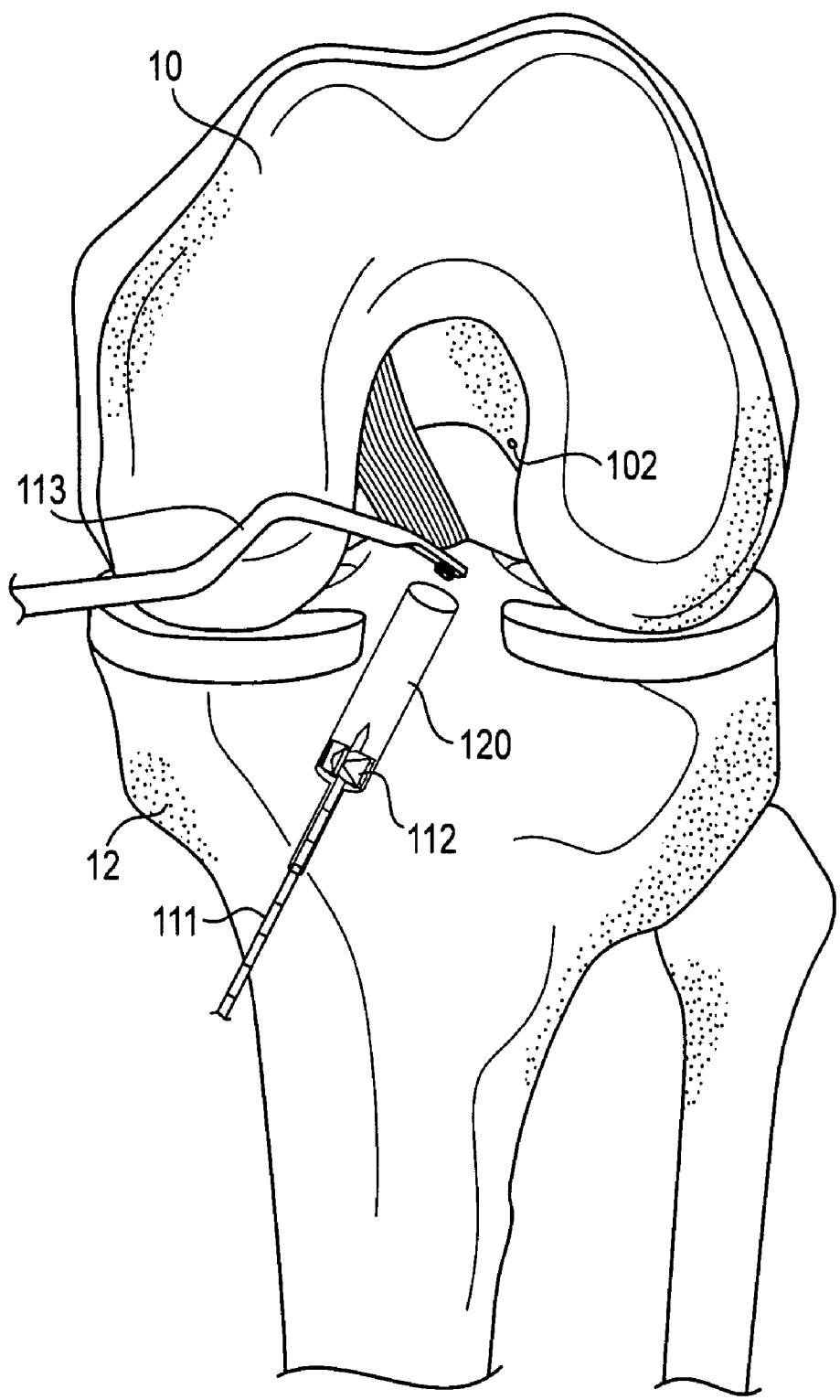
FIG. 5 schematically illustrates the formation of a tibial socket in accordance with the present invention.

The drill depth grommet 114 is advanced to the end of the guide pin sleeve 115 for socket depth assessment during drilling, as is illustrated in FIGS. 4A and 4B. Referring to FIG. 5, once securely engaged with the rotary drill cutter 112, the rotary drill pin 111 is rotated with a powered drill (not shown) and forward (clockwise) drilling, with slight retrograde force, facilitates retrograde drilling of the tibial socket 120 to the appropriate depth of 30 to 40 mm. The calibrated pin 111 and grommet 114 provides precise visual depth control (FIGS. 4A and 4B). Antegrade (e.g., forward) tapping of the powered drill pushes the cutter 112 out the tibial socket 120 and into the joint space. The drill guide 110 is then removed.

Figure 6:
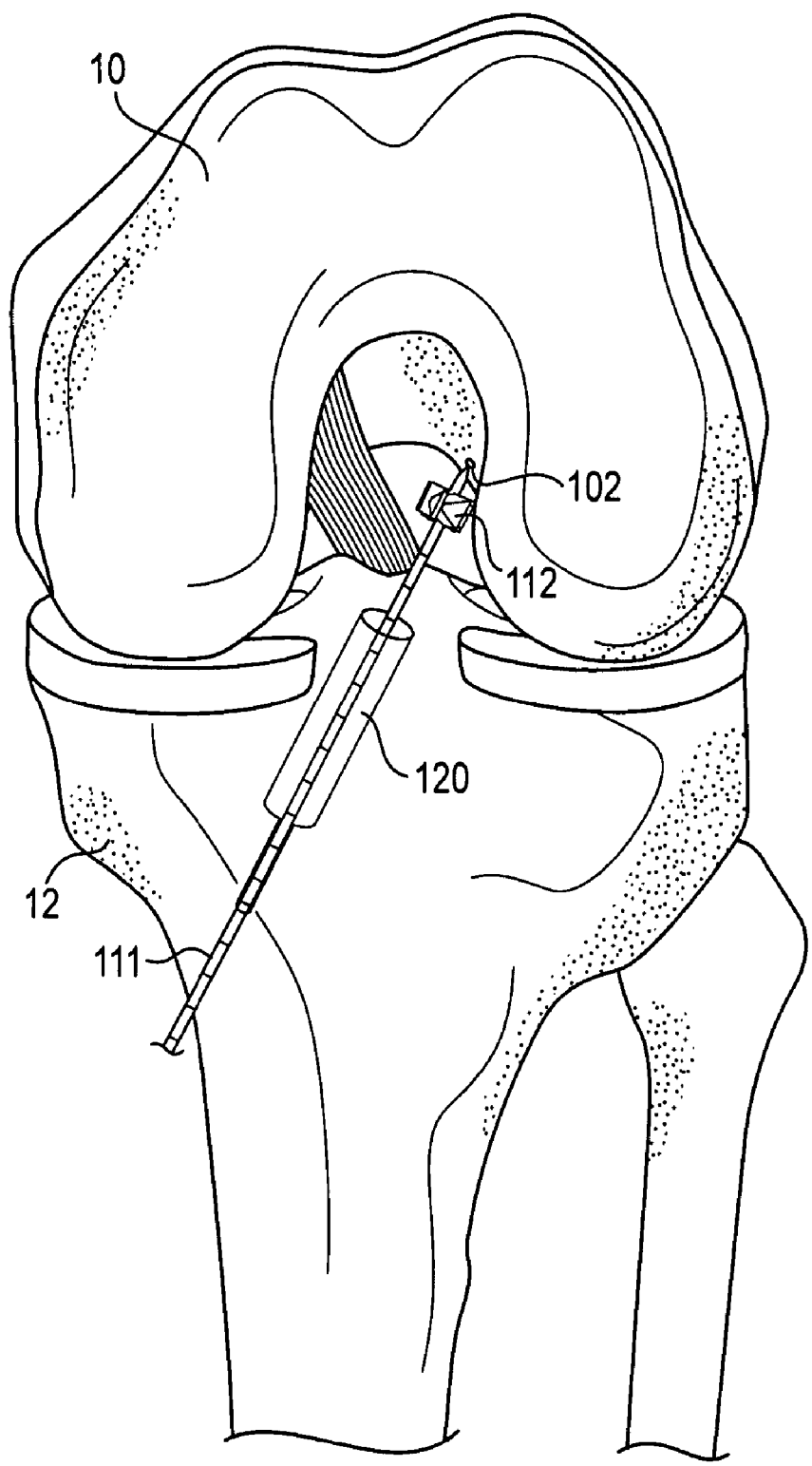
FIG. 6 schematically illustrates the alignment of the dual-sided rotary drill cutter for formation of a femoral socket in accordance with the present invention.
Figure 7:
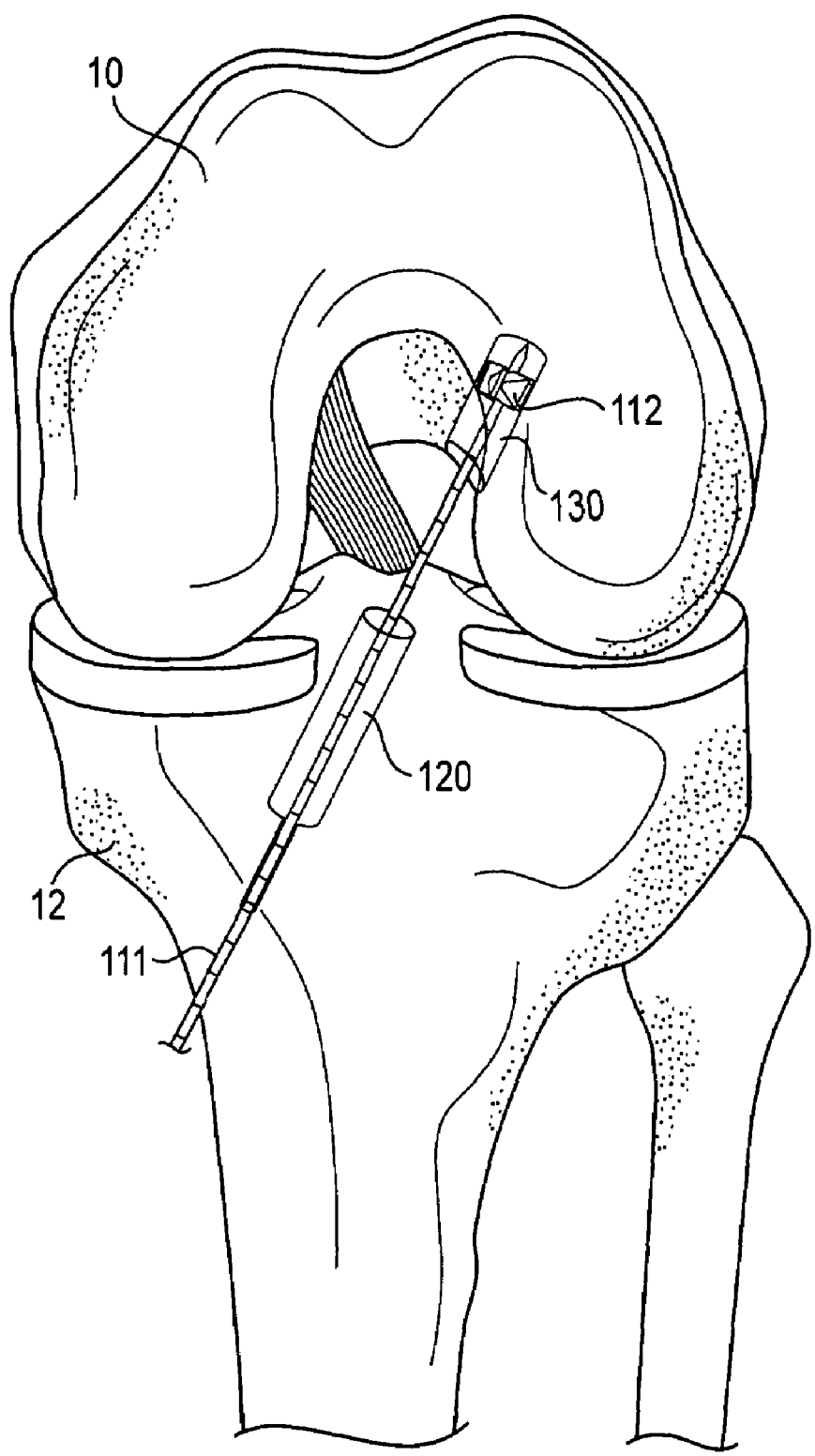
FIG. 7 schematically illustrates the formation of a femoral socket in accordance with the present invention.

As shown in FIG. 6, the dual rotary drill cutter 112 is then advanced forward so that the tip of the rotary drill pin 111 is placed into the reference position 102 created with the transtibial drill guide 101. Care is taken to advance the cutter past the PCL, so as not to cause damage to the PCL. In preferred embodiments, extension of the knee facilitates pin engagement in the femoral reference position 102. Then, as shown in FIG. 7, forward drilling, with slight antegrade force, advances the cutter 112 to create a 30 mm femoral socket 130 with depth control confirmed with the calibrated pin 111 and depth grommet 114. Reverse tapping of the powered drill extracts the cutter 112 from the femoral socket 130.

In an alternative embodiment of the invention, the rotary drill guide pin 111 may include a non-rigid section so that the femoral socket 130 may be drilled more horizontally as compared to the tibial socket 120. This may or may not be used in conjunction with a guide inserted through the medial portal.

Once the femoral socket 130 is cut, the rotary drill cutter 112 is retracted carefully past the PCL to the tibial plateau. Once both the tibial and femoral sockets 120, 130, the rotary drill cutter 112 may be removed. The cutter 112 may be removed in the opposite fashion by which it was inserted, as shown in FIGS. 8A and 8B; the cutter 112 is threaded back onto the threads 116 of the insertion post 113 and removed from the joint. Alternatively, the rotary drill cutter 112 is securely engaged with a grasper 116 and the pin 111 is drilled in reverse to disengage the threaded pin 111 from the rotary drill cutter 112, as shown in FIGS. 8C and 8D.

The advantage of drilling the tibial and femoral sockets 120, 130 with a dual-sided rotary drill cutter 112 is that it is not necessary to flip the rotary drill cutter 112 between formation of the sockets 120, 130. In the '044 application, the rotary drill cutter 112 must be removed from the rotary drill pin 111 between formation of the tibial and femoral sockets 120, 130 in order to place the cutting teeth in the correct direction. By making the rotary drill cutter 112 dual-sided, this is no longer necessary and limits the possibility that the rotary drill cutter 112 will become lost while being flipped.

Figure 12:
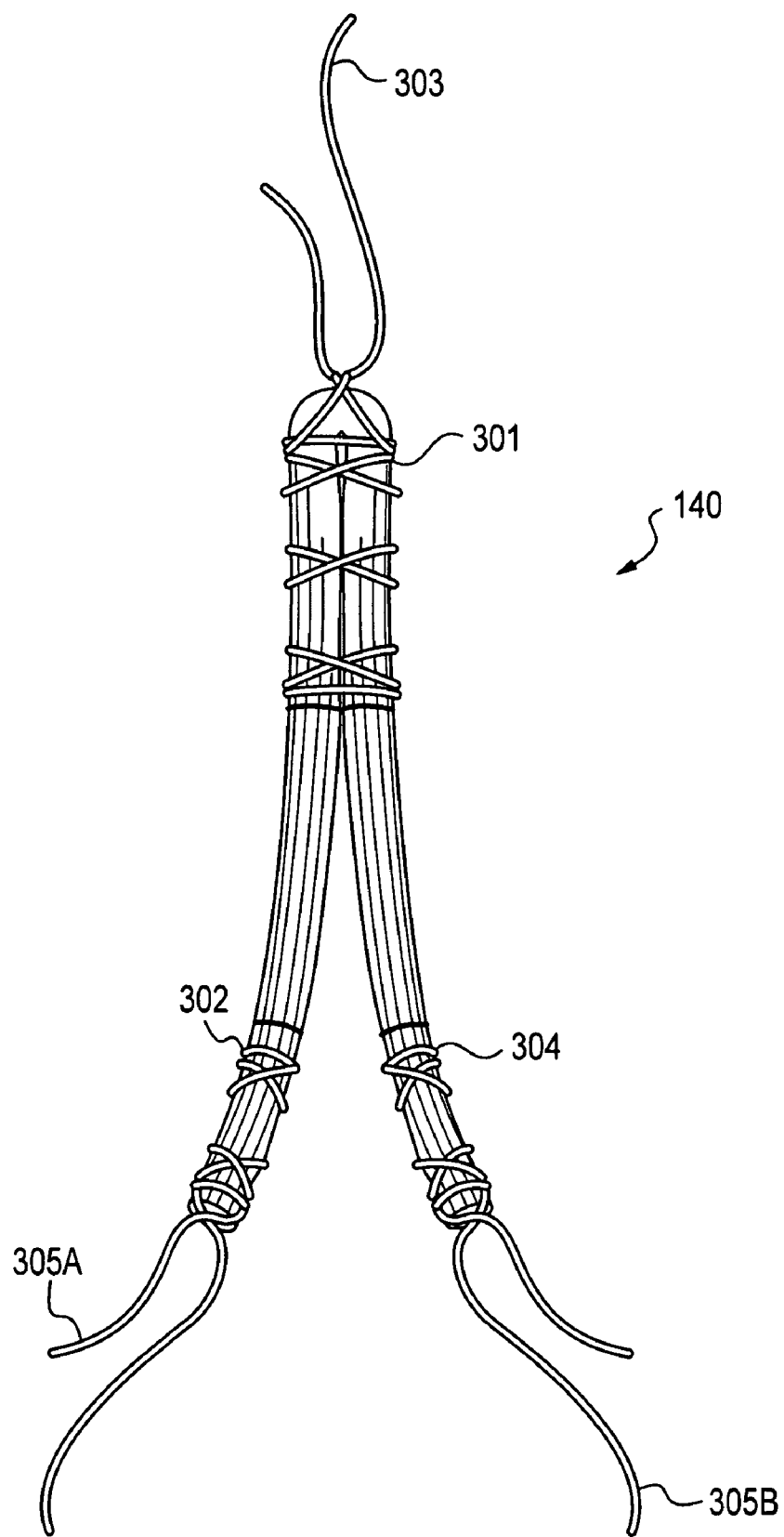
FIG. 12 illustrates a graft in accordance with the present invention.

A graft 140, illustrated in FIG. 12, is then prepared for insertion and fixation into the femoral and tibial sockets 130, 120. The graft 140 is prepared to a length that is 10 mm less than the total overall depth of the sockets and the intraarticular distance between the sockets (i.e. 30+30+40=100 mm). The graft length must be 10 mm less (i.e. 90 mm or less) than the overall socket and joint distance to properly tension the graft 140 during fixation.

Graft 140 is formed from soft tissue, according to an exemplary embodiment of the present invention. The graft 140 is folded in half and whip stitched at the graft proximal end 301 and distal bundle ends 302, 304. Each of the ends of the graft 140 is securely whip-stitched independently with one set of strands 303 and another set of strands 305A and 305B, as illustrated in FIG. 12. The diameter of the graft 140 is measured before drilling, for example using a graft sizing block (not shown), to determine the required diameter of the femoral and tibial sockets 130, 120 and to determine the appropriate sized dual rotary drill cutter 112.

A suture loop with a free floating needle, such as disclosed in U.S. Provisional Application Ser. No. 60/834,191, filed Jul. 31, 2006, entitled "Suture Loop with Free Floating Needle," and U.S. application Ser. No. 11/723,512 (claiming the benefit of U.S. Provisional Application Ser. No. 60/783,866, filed Mar. 21, 2006) entitled, "Whipstitched Graft Construct and Method of Making Same," facilitates rapid, atraumatic whipstitching of the graft ends on the graft prep workstation. The entirety of these applications are incorporated herein by reference.

Figure 10:
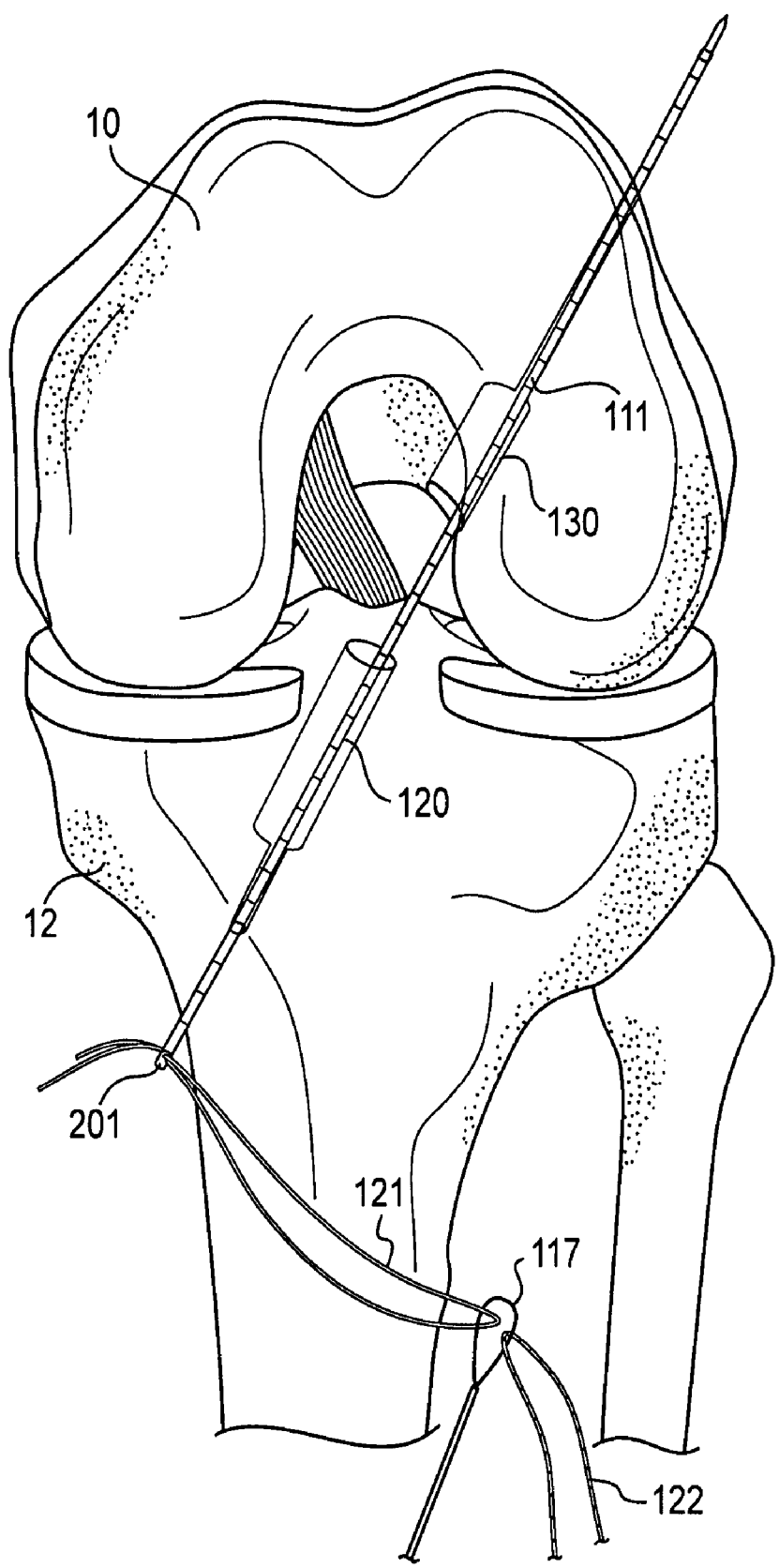
FIG. 10 schematically illustrates a rotary drill guide pin passing through the sockets in preparation for graft insertion in accordance with the present invention.
Figure 11A:
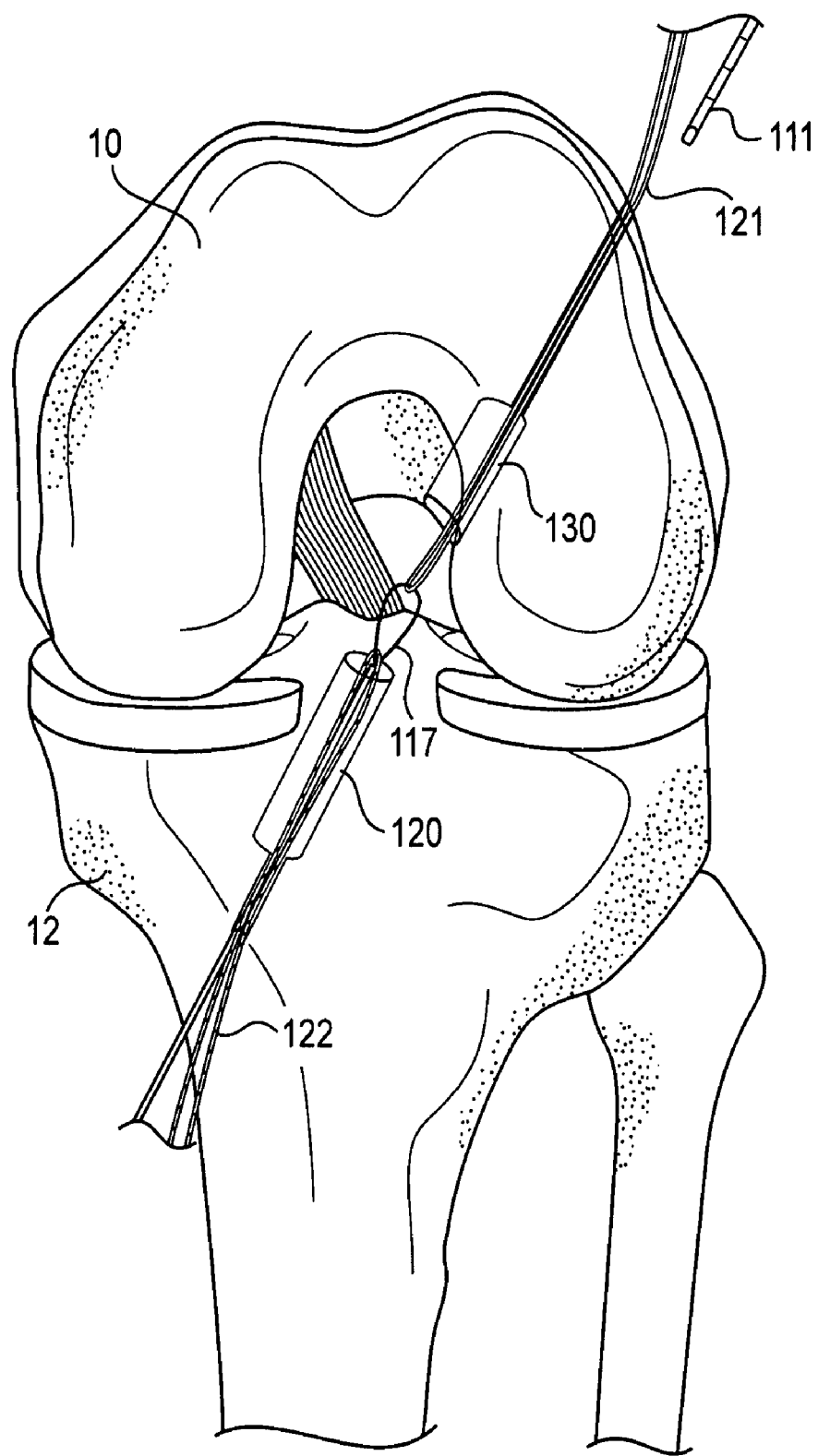
FIGS. 11A-11E schematically illustrate the graft insertion process in accordance with the present invention.
Figure 11B:
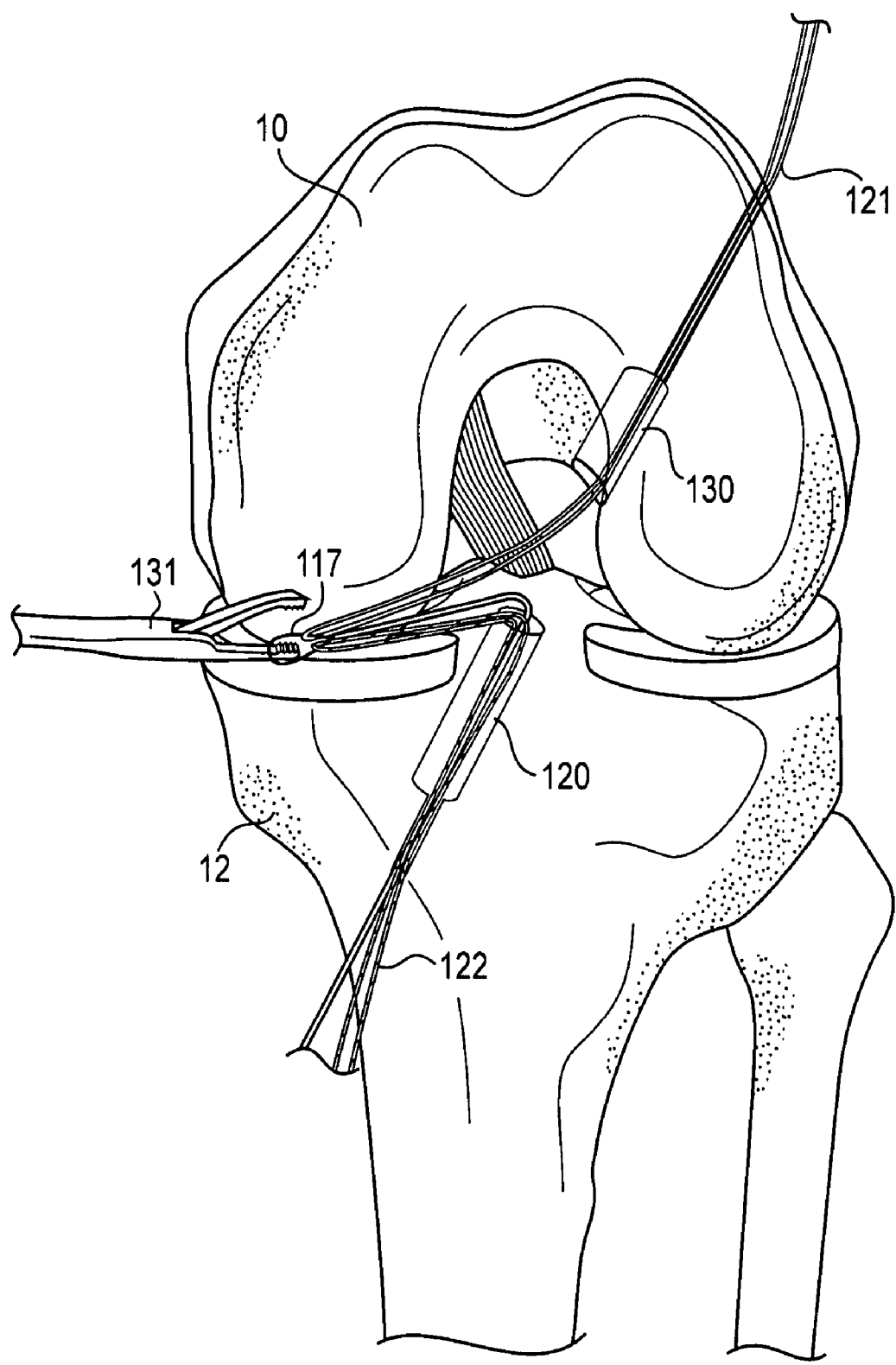
Figure 11C:
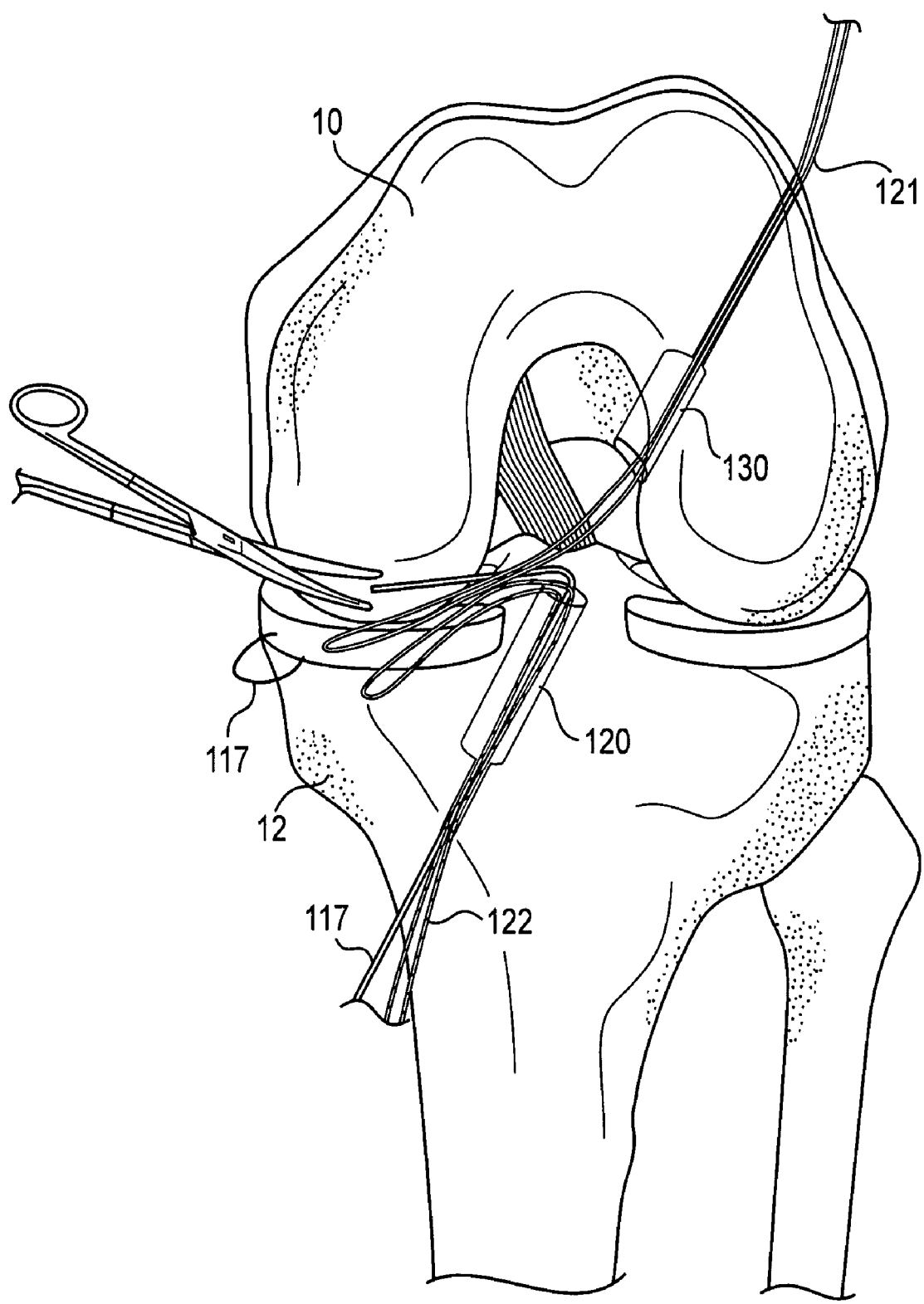
Figure 11D:
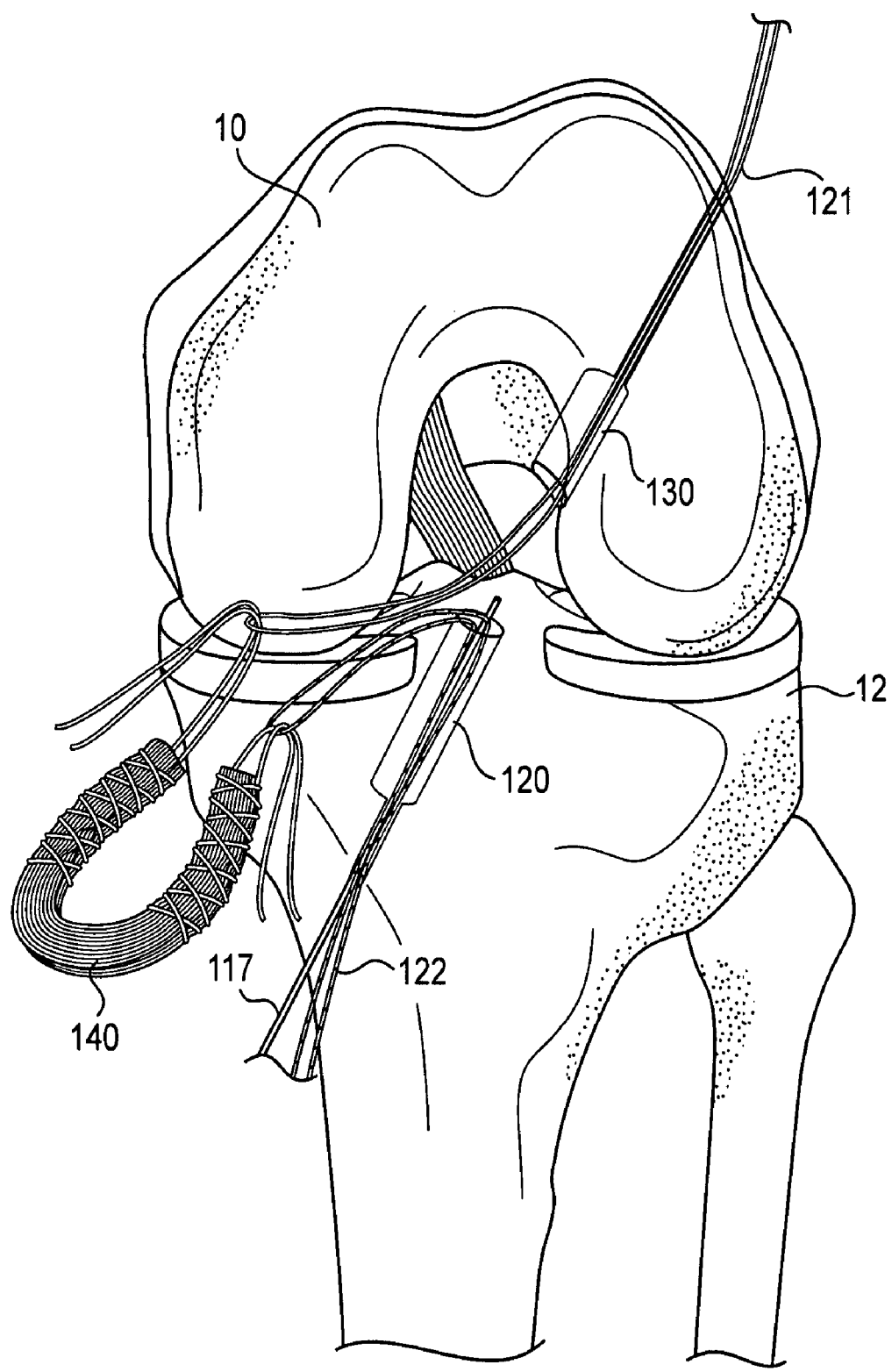
Figure 11E:
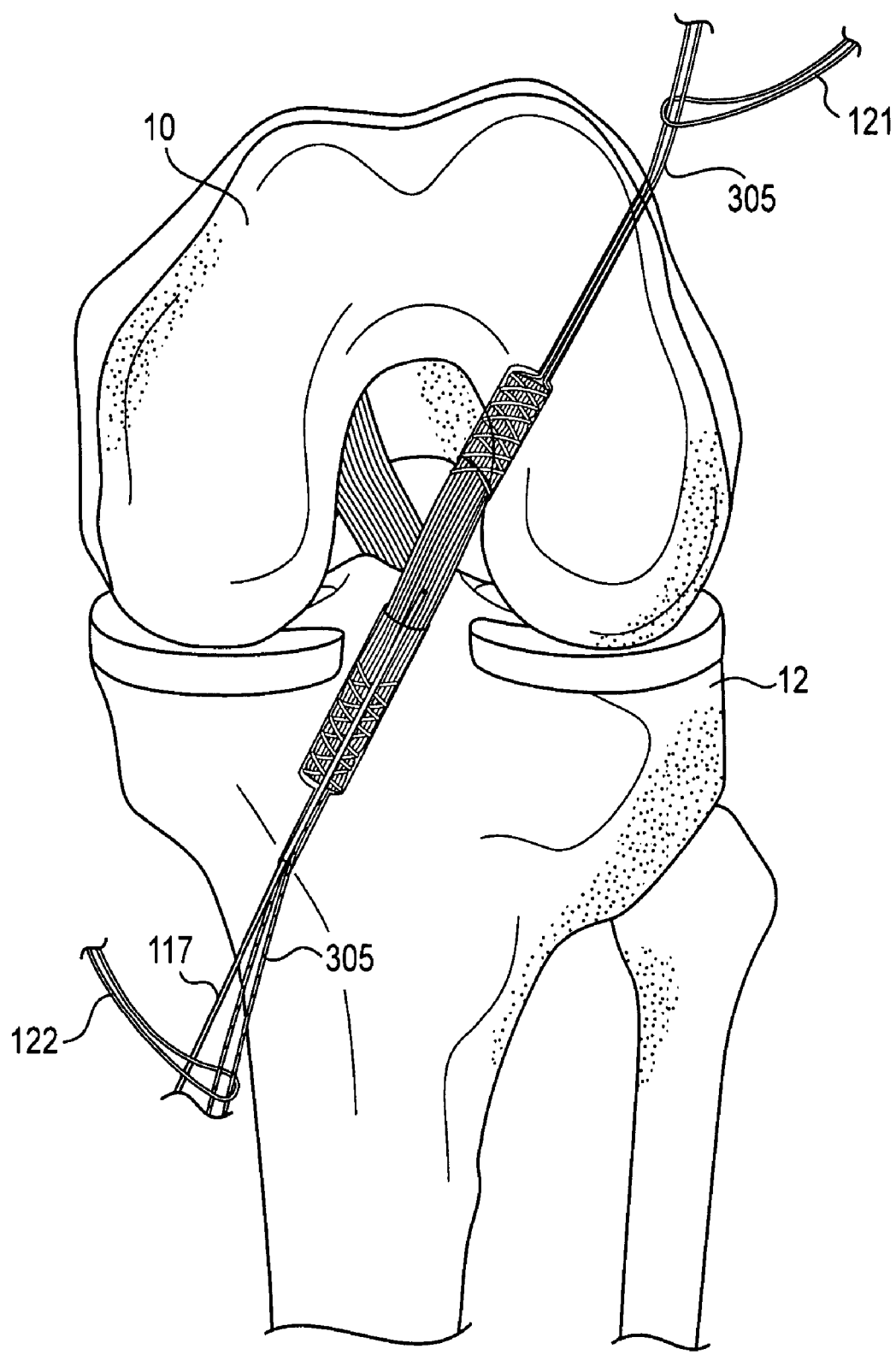

Installation of the graft 140 is illustrated schematically in FIGS. 10-12. A graft passer is easily assembled by inserting a plain suture 121 (preferably a high strength suture, such as FiberWire suture, sold by Arthrex, Inc. of Naples, Fla.) and a striped suture 122 (also preferably a high strength suture, such as TigerWire suture, sold by Arthrex, Inc.) into a looped nitinol wire 117, as shown in FIG. 10. The graft passer is passed across the joint using a rotary drill guide pin 111 (shown in more detail in FIGS. 9A-9D). The plain suture 121 is inserted into the angled slot 201 at the distal end of the guide pin 111, shown in FIGS. 9C and 10C. The rotary drill guide pin 111 is then passed through the sockets 120, 130 and out the lateral thigh. Upon exiting the femur 10, the rotary drill guide pin 111 is disconnected and the tail ends of the plain suture 121 are retrieved, as shown in FIG. 11A. The loop is then pulled back into the knee and retrieved out the anteromedial portal using a grasper 131, as shown in FIG. 11B. The nitinol wire 117 loop is then cut as shown in FIG. 11C, separating the loops for graft suture passing into respective femoral (plain suture) and tibial (striped suture) sockets 130, 120 through the anteromedial portal. The remaining nitinol wire 117 stays in the tibial socket 120. The graft 140 is attached to the loops 121, 122 as shown in FIG. 11D. The femoral end of the graft 140 is passed using the plain suture 121 loop and the tibial end is passed using the striped suture 122 loop, as shown in FIG. 11E. Methylene blue markings and the location of the suture loop confirms balanced insertion of the graft 140 ends into the sockets 120, 130. Care should be taken to maintain an anterior position of the nitinol wire 117 in the tibial socket 120 during graft 140 passing and positioning.

FIGS. 13-18 illustrate fixation of the graft 140 using retroscrew technology. It should be noted however, that the dual sided retrocutter technique of forming sockets 120, 130 may be used with alternative methods of graft fixation. The nitinol wire 117 facilitates insertion of the thin diameter retroscrew driver up the tibial rotary drill guide pin 111 hole, anterior to the graft 140. The retroscrew driver 141 and sutures, etc, used in the retroscrew technology are inserted through the 3 mm distal guide pin hole, and therefore a transtibial tunnel is not required.

Figure 13A:
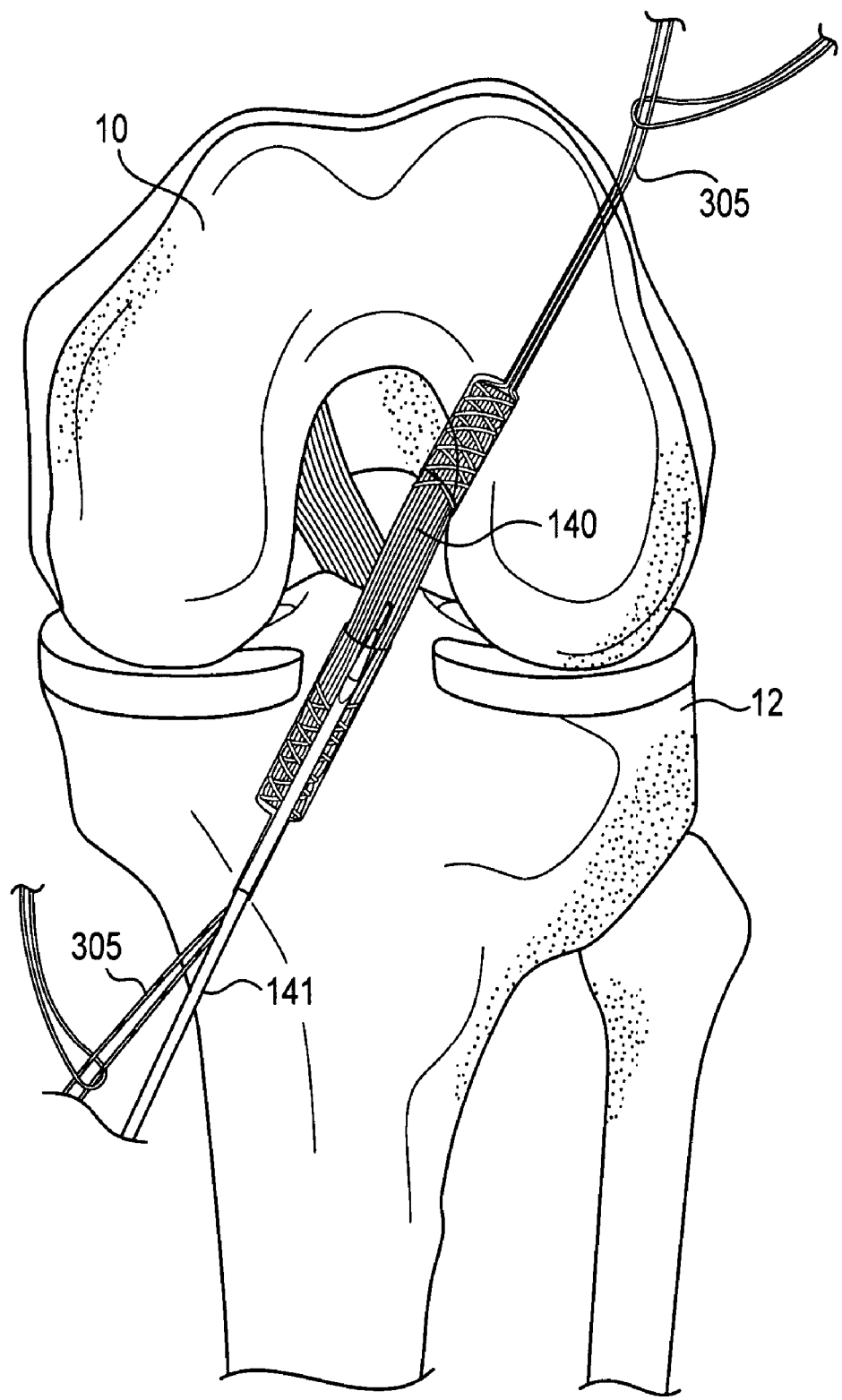
FIGS. 13A-13B illustrates a schematic view of a knee joint undergoing graft fixation in accordance with the present invention.
Figure 13B:
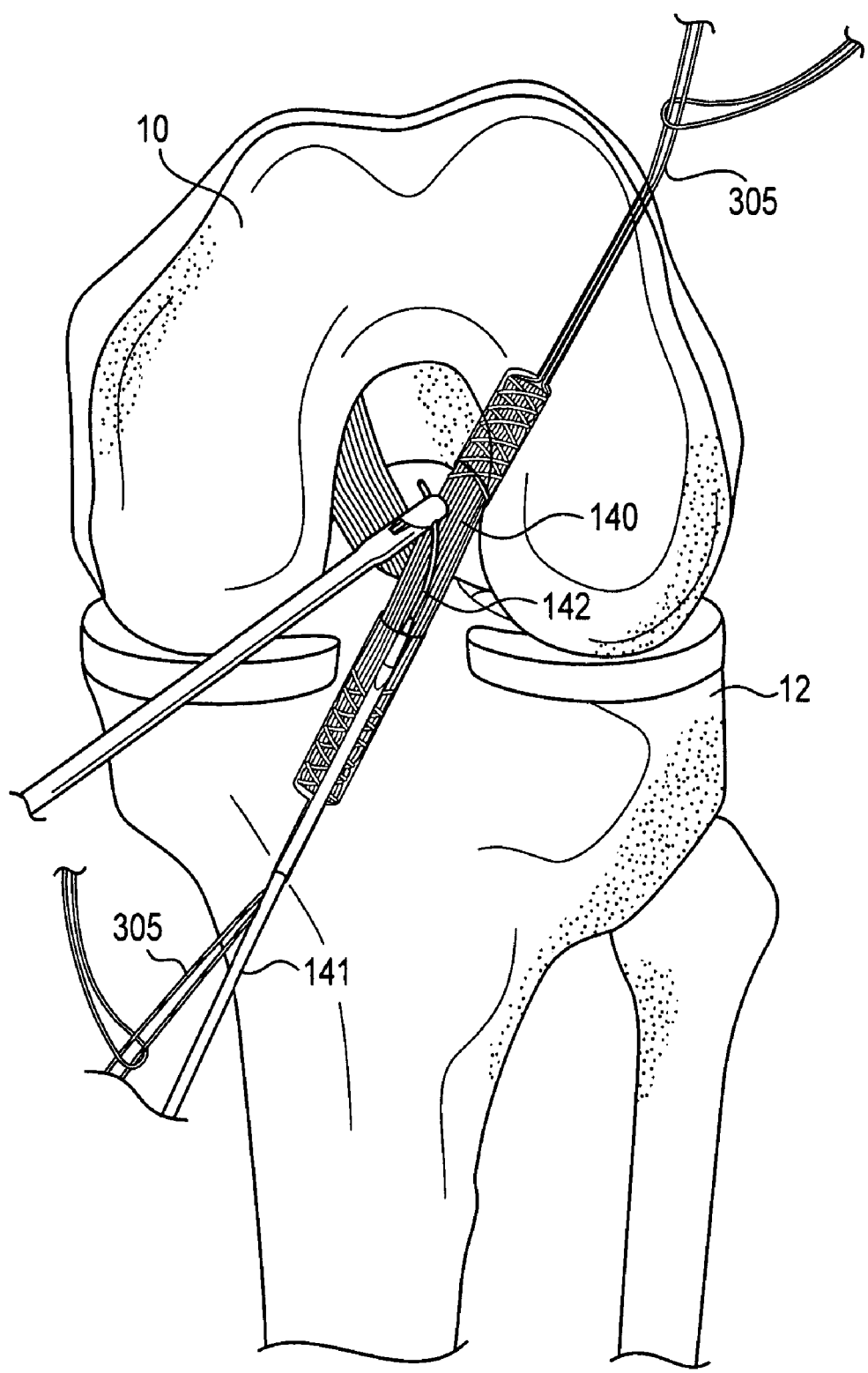
Figure 14:
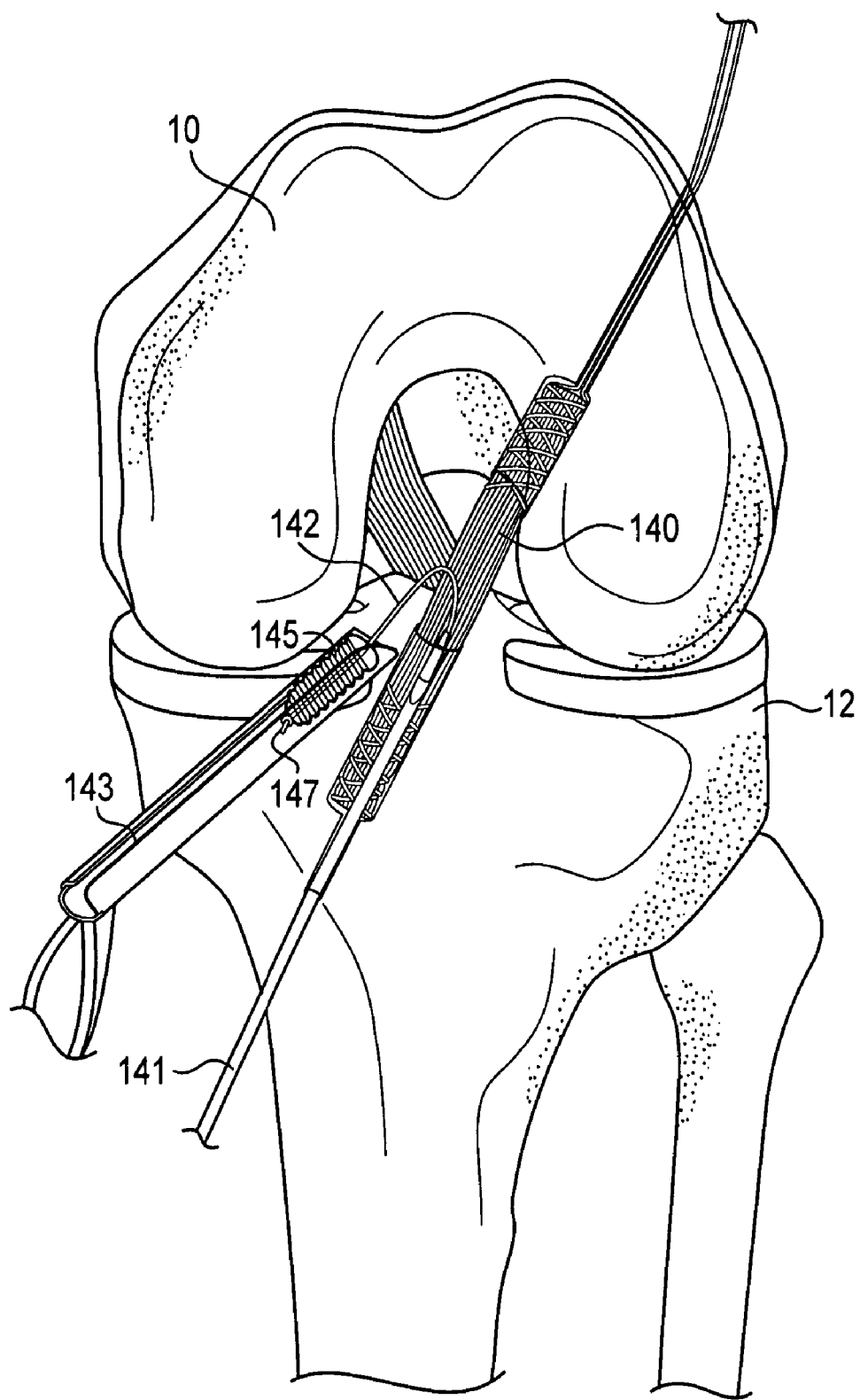
FIG. 14 illustrates a schematic view of the knee joint of FIG. 14 at a stage of graft fixation subsequent to that shown in FIG. 13.

As shown in FIG. 13A, the 3 mm diameter retroscrew driver 141 is inserted over the nitinol guide wire 117 through the 3 mm distal guide pin hole and tibial socket 120, anterior to the graft 140. The nitinol wire 117 is removed from the retroscrew driver 141. As shown in FIG. 13B, a retroscrew tether suture 142 is passed through the cannulation of the screwdriver 141. The suture 142 is passed through the appropriate diameter femoral retroscrew 145, where a large knot 147 is tied. The femoral retroscrew 145 is pulled though the anteromedial portal into the joint with the shoehorn cannula 143 as shown in FIG. 14.

Figure 15:
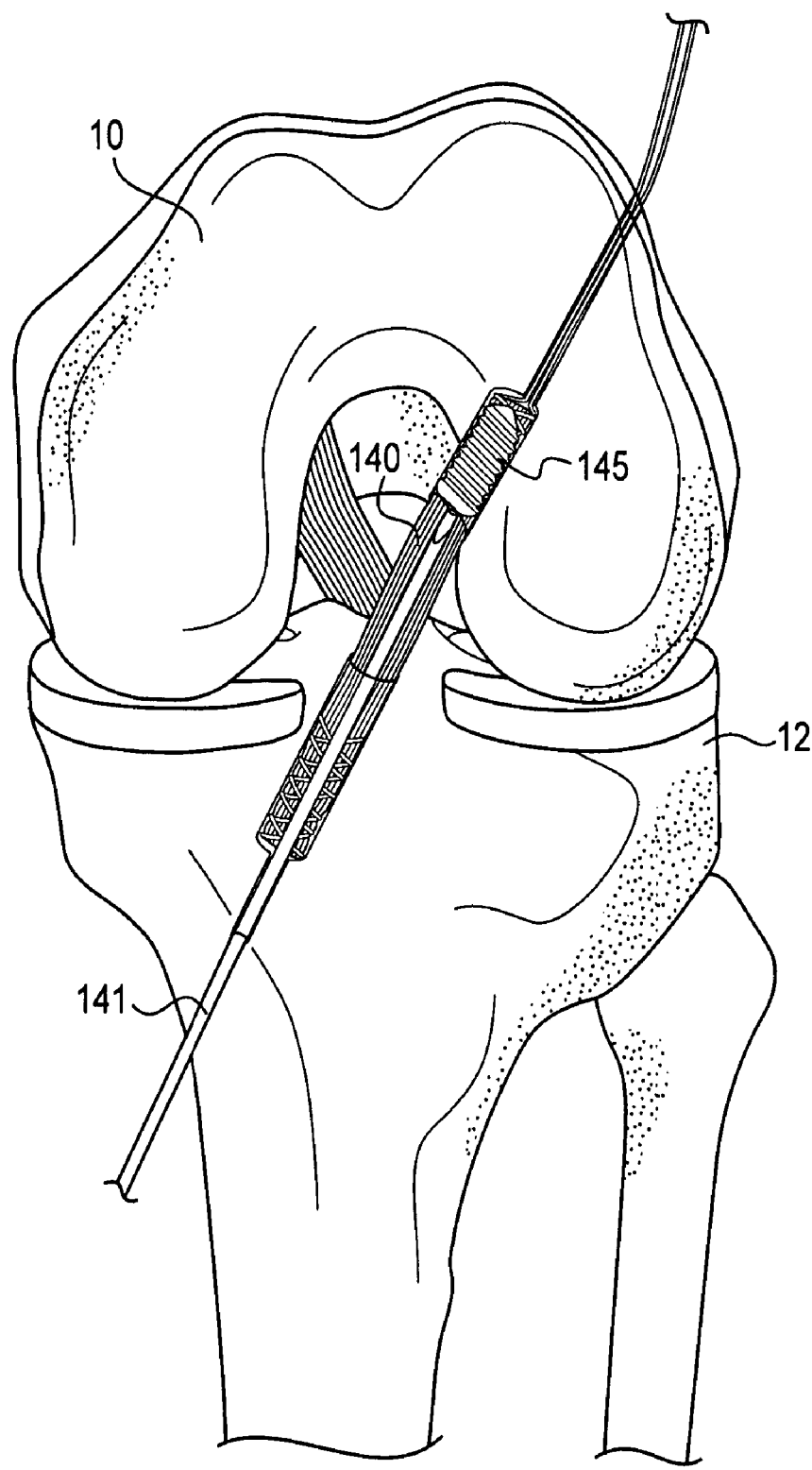
FIG. 15 illustrates a schematic view of the knee joint of FIG. 14 at a stage of graft fixation subsequent to that shown in FIG. 14.

The retroscrew driver 141 tip is retracted to the rim of the tibial socket 120 and the femoral retroscrew 145 mounted onto the driver tip with the suture tether 142. The screwdriver 141 is fully engaged into the screw 145, the tether suture 142 removed and the screw 145 advanced to the femoral socket 130 parallel the graft 140, as shown in FIG. 15. The retroscrew 145 is inserted medial and superior to the graft 140. The suture 142 is removed before inserting the screw 145.

Figure 16:
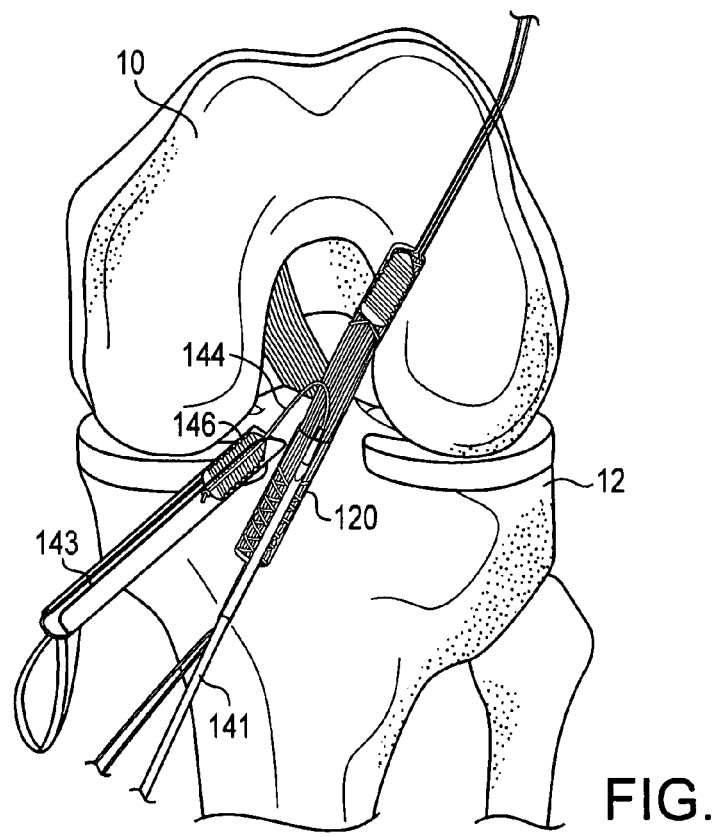
FIG. 16 illustrates a schematic view of the knee joint of FIG. 14 at a stage of graft fixation subsequent to that shown in FIG. 15.

As shown in FIG. 16, the retroscrew driver 141 tip is retracted to the rim of the tibial socket 120 and a stiff suture 144 (such as Fiberstick suture, sold by Arthrex, Inc.) is inserted from distal to proximal through the screwdriver 141 cannulation. The stiff suture end is retrieved out the anteromedial portal and attached to the appropriate diameter tibial retroscrew 146 with a Mulberry knot. The tibial retroscrew 146 is pulled onto the screwdriver 141 tip with shoehorn cannula 143 insertion.

Figure 17:
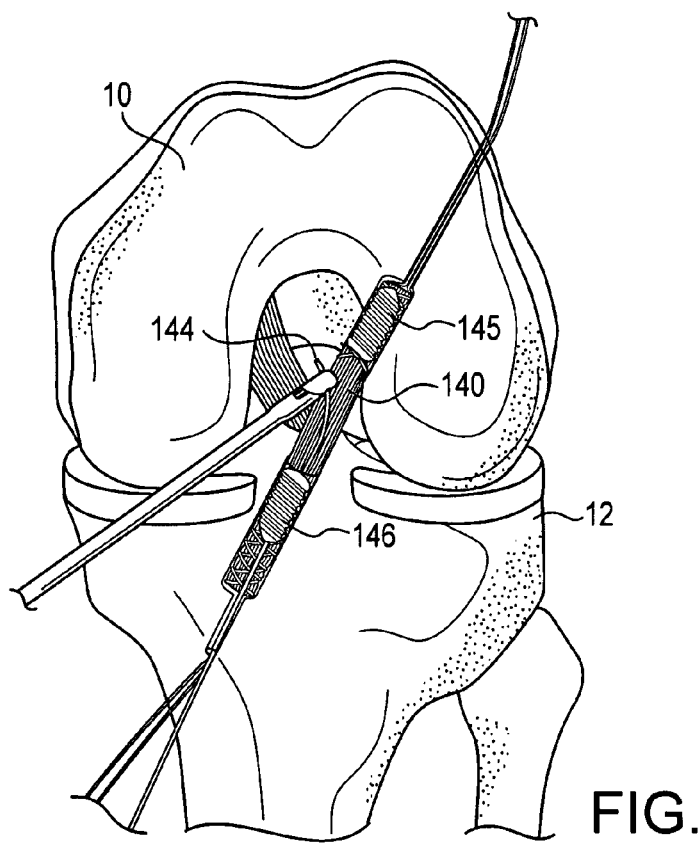
FIG. 17 illustrates a schematic view of the knee joint of FIG. 14 at a stage of graft fixation subsequent to that shown in FIG. 16.

The knee is brought into near extension, the graft 140 appropriately tensioned, and the tibial retroscrew 146 inserted with reverse rotation fully into the tibial socket 120, as shown in FIG. 17. The tether suture 144 is then removed.

Figure 18A:
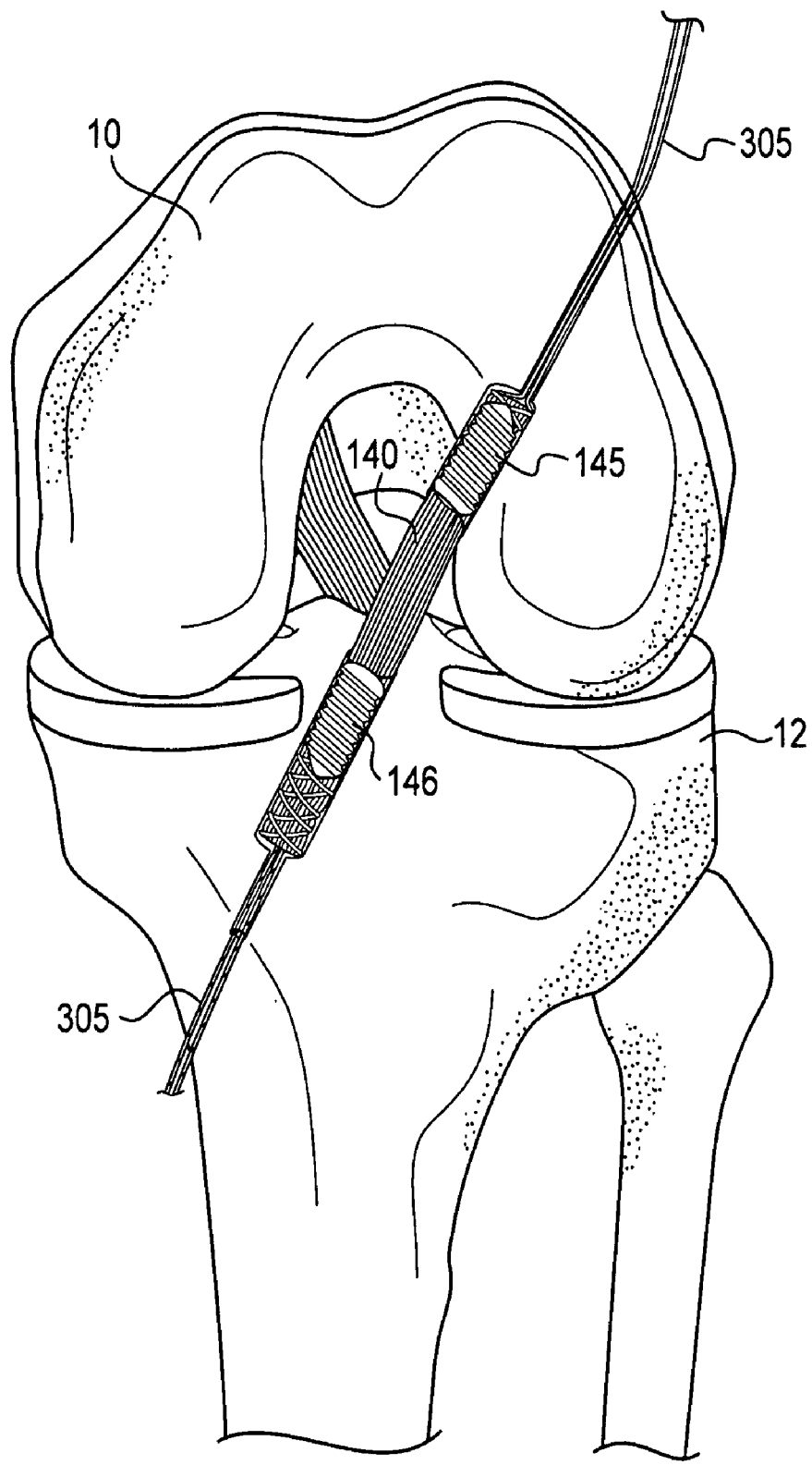
FIGS. 18A-18C illustrate a schematic view of a knee joint having undergone knee reconstruction surgery in accordance with the present invention.
Figure 18B:
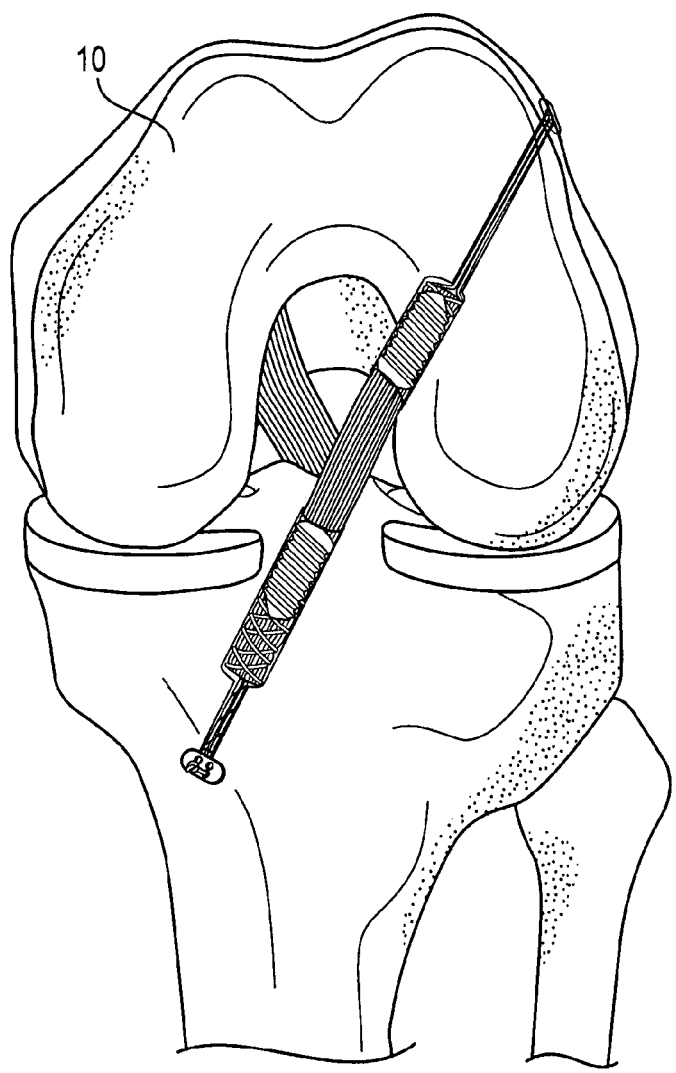
Figure 18C:
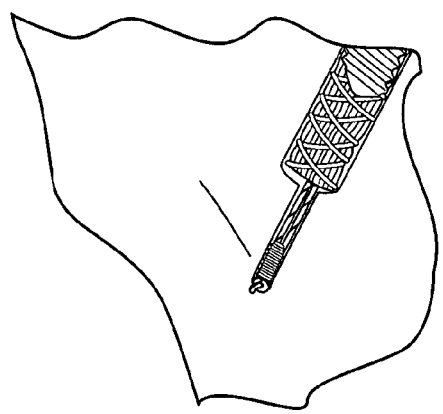

FIG. 18A illustrates the final ACL reconstruction. FIG. 18B illustrates a backup fixation formed with 2 hole PEEK or titanium buttons 150 over the exit hole. Alternatively, the backup fixation may be achieved with suture knots tied over the head of a 3 mm×10 mm Biotenodesis screw inserted into the 3 mm hole parallel to the sutures, as shown in FIG. 18C.

While described embodiments have been described in detail, it should be readily understood that the invention is not limited to the disclosed embodiments. Rather the embodiments can be modified to incorporate any number of variations, alterations, substitutions or equivalent arrangements not heretofore described.

What is claimed as new and desired to be protected by Letters Patent of the United States is:

1. A method of knee reconstruction comprising:
    inserting a guide pin through a tibia;
    attaching a dual-sided rotary cutter to the guide pin;
    forming a tibial socket in the tibia by retrograde drilling;
    forming a femoral socket in a femur by antegrade drilling, wherein the dual-sided rotary cutter is not removed from the guide pin between formation of the respective sockets; and
    securing the ends of a graft respectively in the sockets of the tibia and femur.

2. The method of claim 1 wherein the guide pin comprises a flexible portion such that the femoral socket may be formed at an angle with respect to the tibial socket.

3. The method of claim 1 wherein forming the femoral socket further comprises aligning the guide pin using a pilot hole formed using a transtibial guide.

* * * * *